(12) United States Patent
Schaffran et al.

(10) Patent No.: US 8,282,395 B2
(45) Date of Patent: Oct. 9, 2012

(54) METHOD OF INSTALLING A PROSTHESIS IN A JAWBONE OF A PATIENT

(75) Inventors: Allan Schaffran, Toronto (CA); Andy Doug-Lun Wong, Toronto (CA); Robert G. Dickie, King City (CA)

(73) Assignee: Pure Dental Logic Inc., Toronto (CA)

( * ) Notice: Subject to any disclaimer, the term of this patent is extended or adjusted under 35 U.S.C. 154(b) by 0 days.

(21) Appl. No.: 12/886,682

(22) Filed: Sep. 21, 2010

(65) Prior Publication Data

US 2011/0008752 A1 Jan. 13, 2011

Related U.S. Application Data

(62) Division of application No. 11/644,719, filed on Dec. 22, 2006, now Pat. No. 7,806,692.

(51) Int. Cl.
*A61C 8/00* (2006.01)
(52) U.S. Cl. ....................................................... 433/173
(58) Field of Classification Search .................... 433/72, 433/75, 141, 153–154, 162–163, 172–176, 433/214–215, 218, 223
See application file for complete search history.

(56) References Cited

U.S. PATENT DOCUMENTS

| | | | |
|---|---|---|---|
| 1,127,236 A | 2/1915 | Harbridge | |
| 1,712,196 A | 5/1929 | Burger et al. | |
| 3,604,488 A | 9/1971 | Wishart et al. | |
| 4,704,929 A | 11/1987 | Osada | |
| 4,744,273 A | 5/1988 | Bartok, Jr. | |
| 5,055,047 A * | 10/1991 | Names | 433/214 |
| 5,158,458 A | 10/1992 | Perry | |
| 5,350,297 A * | 9/1994 | Cohen | 433/76 |
| 5,423,860 A | 6/1995 | Lizardi et al. | |

(Continued)

FOREIGN PATENT DOCUMENTS

WO 97/06930 2/1997

(Continued)

OTHER PUBLICATIONS

Mark Hafwell D.D.S. M.S.C., Dental Implants: A Different Perspective (Part 2), Implant Practice, US Edition, May 2009, vol. 2, No. 2, pp. 34-41.

*Primary Examiner* — Todd Manahan
*Assistant Examiner* — Matthew Nelson
(74) *Attorney, Agent, or Firm* — Sand & Sebolt

(57) ABSTRACT

An abutment clip for use in a dental implant system for orienting an abutment relative to features on a patient's teeth and jawbone so that a prosthesis, which is attachable to the abutment, will be correctly oriented. The abutment clip comprises a housing that includes a chamber sized to receive the abutment therein. The housing has at least one position indicator provided at one end thereof. The dentist engages the abutment clip over the abutment when it is still attached to a manufacturer's plaster model. He notes the position of the indicator on the housing in reference to features on the model and then detaches the abutment clip, abutment and abutment screw as a unit from the model. The combined abutment clip, abutment and screw are then positioned on an implant post in the patient's jaw bone and the position indicator is used to verify the orientation of the abutment before it is secured to the implant post.

22 Claims, 13 Drawing Sheets

U.S. PATENT DOCUMENTS

| | | | |
|---|---|---|---|
| 5,462,436 A * | 10/1995 | Beaty | 433/141 |
| 5,692,904 A * | 12/1997 | Beaty et al. | 433/141 |
| 5,927,979 A | 7/1999 | Misch et al. | |
| 6,116,125 A | 9/2000 | McLeod | |
| 6,227,856 B1 | 5/2001 | Beaty et al. | |
| 6,244,141 B1 | 6/2001 | Han | |
| 6,280,192 B1 | 8/2001 | Groll et al. | |
| 6,328,746 B1 | 12/2001 | Gambale | |
| 6,701,812 B1 | 3/2004 | Sawamura | |
| 6,824,386 B2 * | 11/2004 | Halldin et al. | 433/173 |
| 6,854,972 B1 | 2/2005 | Elian | |
| 6,951,460 B2 * | 10/2005 | Halldin et al. | 433/173 |
| 6,997,086 B1 | 2/2006 | Graham | |
| 7,100,476 B1 | 9/2006 | Feit | |
| 2002/0039717 A1 * | 4/2002 | Amber et al. | 433/172 |
| 2002/0106610 A1 | 8/2002 | Hurson | |
| 2004/0180308 A1 * | 9/2004 | Ebi et al. | 433/173 |
| 2005/0266379 A1 | 12/2005 | Kumar | |
| 2006/0075856 A1 | 4/2006 | Tilton | |
| 2006/0278050 A1 | 12/2006 | Hsiao | |
| 2007/0295173 A1 | 12/2007 | Swartz | |
| 2008/0241789 A1 * | 10/2008 | Mundorf | 433/173 |

FOREIGN PATENT DOCUMENTS

| | | |
|---|---|---|
| WO | 97/24996 | 7/1997 |
| WO | 00/28914 | 5/2000 |
| WO | 03/037207 | 5/2003 |
| WO | 03/101332 | 12/2003 |

* cited by examiner

METHOD OF INSTALLING A PROSTHESIS IN A JAWBONE OF A PATIENT

CROSS REFERENCE TO RELATED APPLICATION

This application is a division of U.S. patent application Ser. No. 11/644,719 filed Dec. 22, 2006; the disclosure of which is incorporated herein by reference.

BACKGROUND OF THE INVENTION

1. Technical Field

This invention generally relates to dentistry. More particularly, the invention relates to dental implants. Specifically, the invention relates to an abutment clip that is detachably engageable over an abutment and includes at least one position indicator thereon that aids the dental surgeon in correctly orienting an abutment on an implant post.

2. Background Information

Over the last few decades dental technology has made great strides in providing improved ways to give people more natural-appearing and better secured artificial teeth or bridgework. (For the sake of clarity, both single artificial teeth and bridgework will be referred to hereinafter as "a prosthesis"). One of those improved technologies utilizes dental implants. A dental implant is a small titanium screw or bolt that is secured into the jaw bone to act as an anchor for a prosthesis. The implants are installed by drilling a small hole in the patient's jaw bone and then screwing an implant post into the bone surrounding the hole. The implant post is then covered with a flap of skin and the patient is sent away for a number of months to allow time for osseointegration to occur, i.e., for the living bone of the jaw to fuse to the implant post. The patient then returns to the dental surgeon who attaches an abutment to the implant post. The abutment is essentially a support that is secured to the implant post and extends upwardly and outwardly away from the jawbone. The prosthesis is then slipped over the abutment and is secured thereover by an adhesive cement.

A number of dental implant systems have been developed by different manufacturers, but most systems provide an implant post that has a specifically shaped post head and an internally threaded bore. The abutment is designed to interlock with the implant post and therefore includes a lower recess that receives the head of the implant post therein. A small screw is then inserted through the abutment and into the bore of the implant post. The screws used in these procedures are very small and are usually only about ¼ inch long. They are therefore extremely difficult to handle as the dental surgeon has to place the screw into a hole on the abutment and then hold both the screw and abutment on the implant post with one finger while trying to line up and begin to engage the threads on the screw with the other hand. Once the thread is started and there is no danger of dropping the screw and abutment, the dental surgeon will use a speed wrench to tighten the screw. When the abutment is secured in place, the prosthesis is attached to the abutment by way of an adhesive cement.

One of the key problems with the above procedure is the extremely limited access in various areas of the mouth, such as the region around the rear molars. The difficulty of this process is further compounded if the position for the implant is in the upper rear part of the mouth between two teeth. This position is more difficult because the dental surgeon faces the effects of gravity and, because the position of installation is toward the back of the mouth, there is the further complication of limited vision and access. If the prosthesis is to be installed between two teeth, the dental surgeon also only has access to the abutment from two sides because of the adjacent teeth. It is easier to position an implant to replace the rearmost molar in the mouth as this location permits the dental surgeon to have access to the abutment from three different sides. The dental surgeon is always concerned that the screw and abutment will fall out of the jawbone before the threads are engaged and that the patient might then accidentally swallow or inhale them. It is therefore commonplace for dental surgeons to position a cloth or other obstruction toward the back of the mouth to catch and retrieve any fallen components. It has been noted by the present inventors that a screw or other small component falls out during the initial thread capture as much as 20% of the time.

A second problem experienced by dental surgeons when doing this procedure is the problem of correctly orienting the abutment during installation so as to ensure that the prosthesis will end up in the correct orientation relative to the surrounding teeth. When either a single artificial tooth or bridgework is to be manufactured, an impression is made of the patient's jawbone after the implant posts have been installed. The impression is used to help the laboratory to produce a model. The model is used to produce a prosthesis that is correctly shaped, positioned and oriented relative to the teeth that are permanently seated in the jawbone. Dental implant systems are made so that the connection between the abutment and the implant post will reduce or prevent any rotation of the prosthesis in the mouth. In order to achieve this, some implant posts are manufactured with hexagonally shaped post heads, some have square post heads and others are triangular. However, this also means that the abutment can be engaged on the post head in more than one orientation. For example, if the abutment/implant connection is triangular in shape, then there are three possible orientations that the abutment may assume on the implant post. If the abutment/implant connection is square in shape, there are four possible positions that the abutment may assume on the implant post head. If the abutment/implant connection is hexagonal, then there are six possible orientations. What is subtle but very important to understand is that the abutment shape is rarely axially aligned with the implant post that is installed in the bone. This is because the implant post will be installed at whatever angle the surgeon feels is the best placement for that bolt in the jawbone. The dental lab must figure out the correct shape and angle that the abutment should be at so as to cause the prosthesis to be correctly aligned in the jawbone with any adjacent teeth. Furthermore, the angle of the abutment also needs to provide the dental surgeon with the necessary clearance to lower and glue the prosthesis into place, while still allowing for sufficient clearance from the adjacent teeth. So the abutment is custom made and carefully oriented on a plaster model.

Once the prosthesis is manufactured, it is returned to the dental surgeon attached to the actual plaster model that was made from the impression. The prosthesis is attached to the plaster model using the custom-made abutment. The dental surgeon has to remove the prosthesis, take special note of the rotational position of the abutment on the model, detach the abutment from the model and then secure the abutment to the implant post in exactly the same rotational position in the patient's jaw. So, if the connection between the abutment and the implant post is a square connection, there will be four different possible positions for the abutment and the dental surgeon has to select the correct one of those four possible positions. This does not sound too difficult, but the abutment is so small and the shape and angle so subtle that it is difficult to get the abutment correctly oriented in the mouth. To make matters worse, the dental surgeon must also control and turn the tiny screw that is inserted through the abutment to set the abutment firmly on the implant post.

There is therefore a need in the art for an improved device, method and system for helping to correctly orient and install dental abutments on implant posts.

SUMMARY OF THE INVENTION

The device of the present invention comprises an abutment clip for use in a dental implant system. The abutment clip is used to orient an abutment relative to features on a patient's teeth and jawbone so that a prosthesis, which is attachable to the abutment, will be correctly oriented. The abutment clip comprises a housing that includes a chamber sized to receive the abutment therein. The housing has at least one position indicator that is provided at one end thereof. The dentist engages the abutment clip over the abutment when it is still attached to a manufacturer's plaster model. He notes the position of the indicator on the housing in reference to features on the model and then detaches the abutment clip, abutment and abutment screw as a unit from the model. The combined abutment clip, abutment and screw are then positioned on an implant post in the patient's jaw bone and the position indicator is used to verify the orientation of the abutment before it is secured to the implant post.

BRIEF DESCRIPTION OF THE DRAWINGS

The preferred embodiments of the invention, illustrative of the best mode in which applicant has contemplated applying the principles, are set forth in the following description and are shown in the drawings and are particularly and distinctly pointed out and set forth in the appended claims.

DETAILED DESCRIPTION OF THE INVENTION

Figure 12:
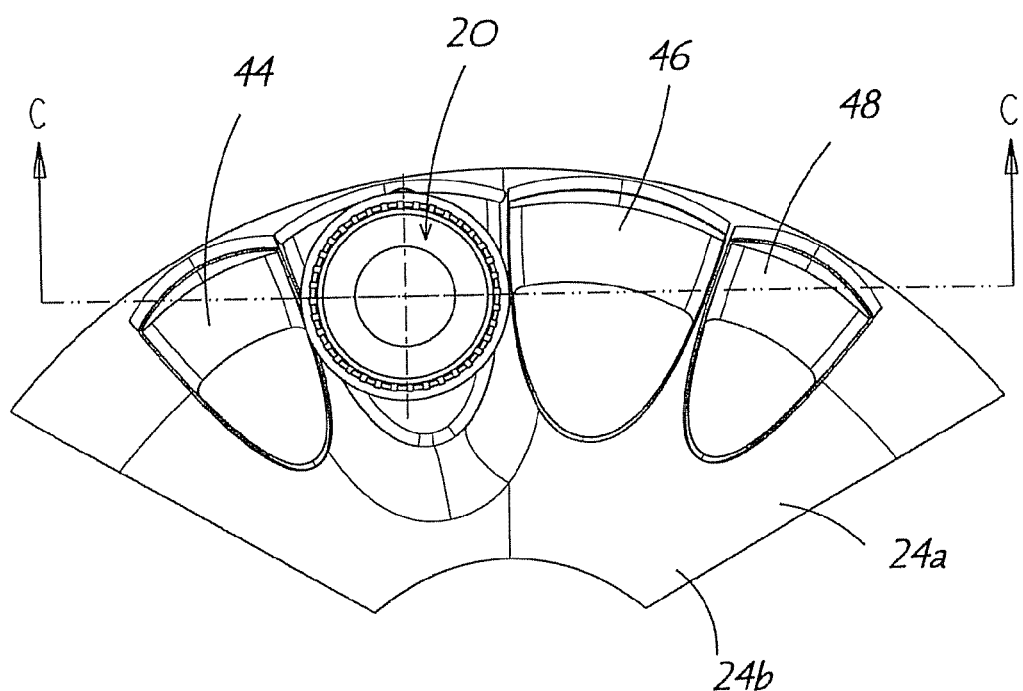
FIG. 12 is a top view of the plaster model or the patient jaw shown in FIG. 11.
Figure 13:
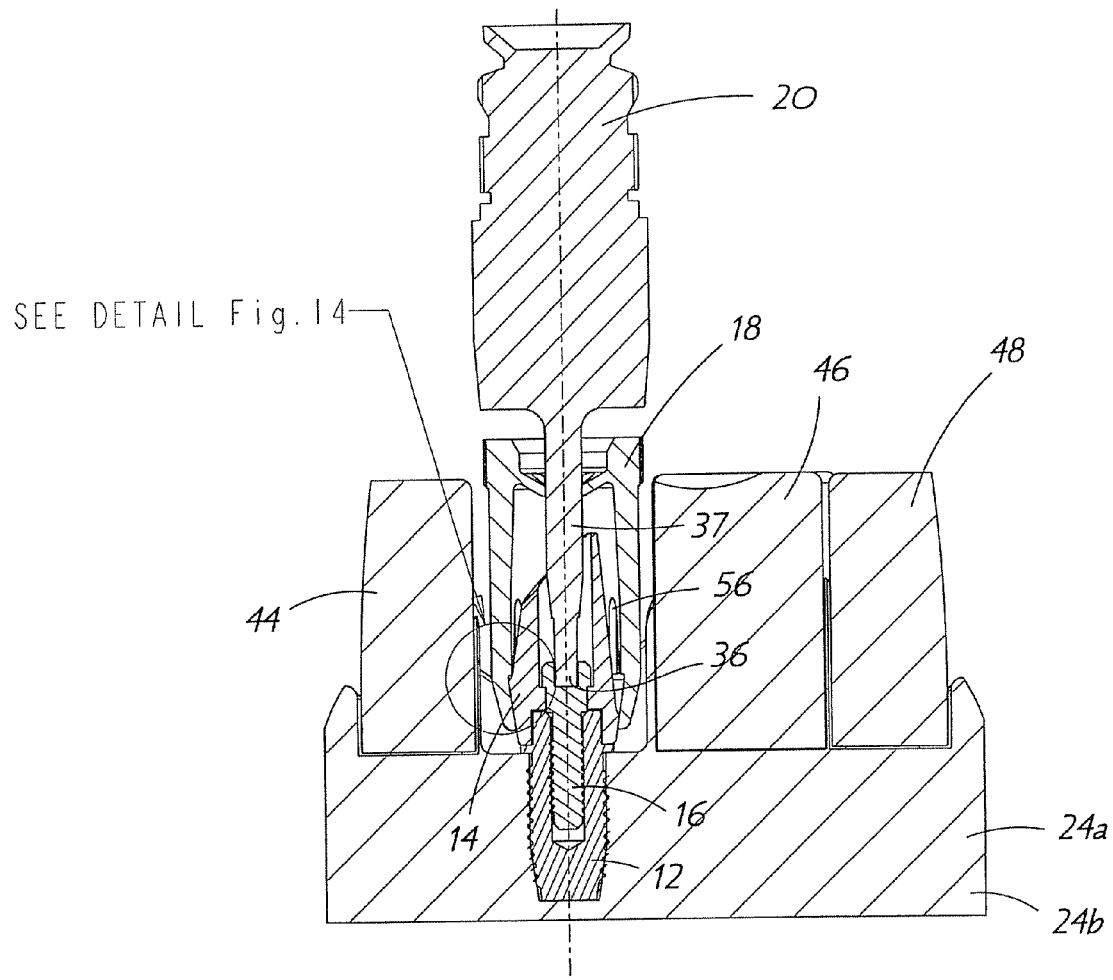
FIG. 13 is a cross-sectional view of the plaster model or the patient jaw through line C-C of FIG. 12.
Figure 14:
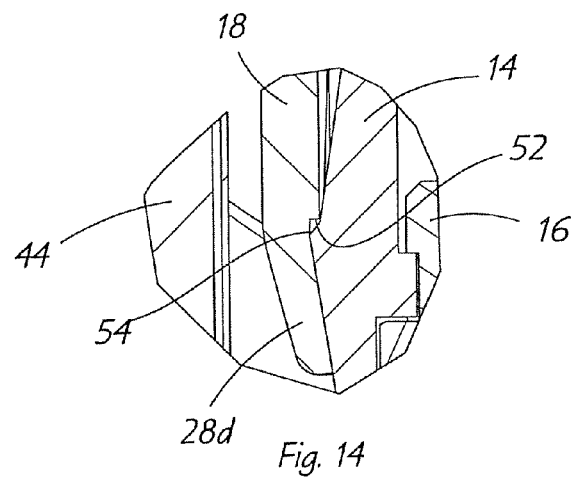
FIG. 14 is an enlarged cross-sectional view of the highlighted region of FIG. 13.
Figure 15:
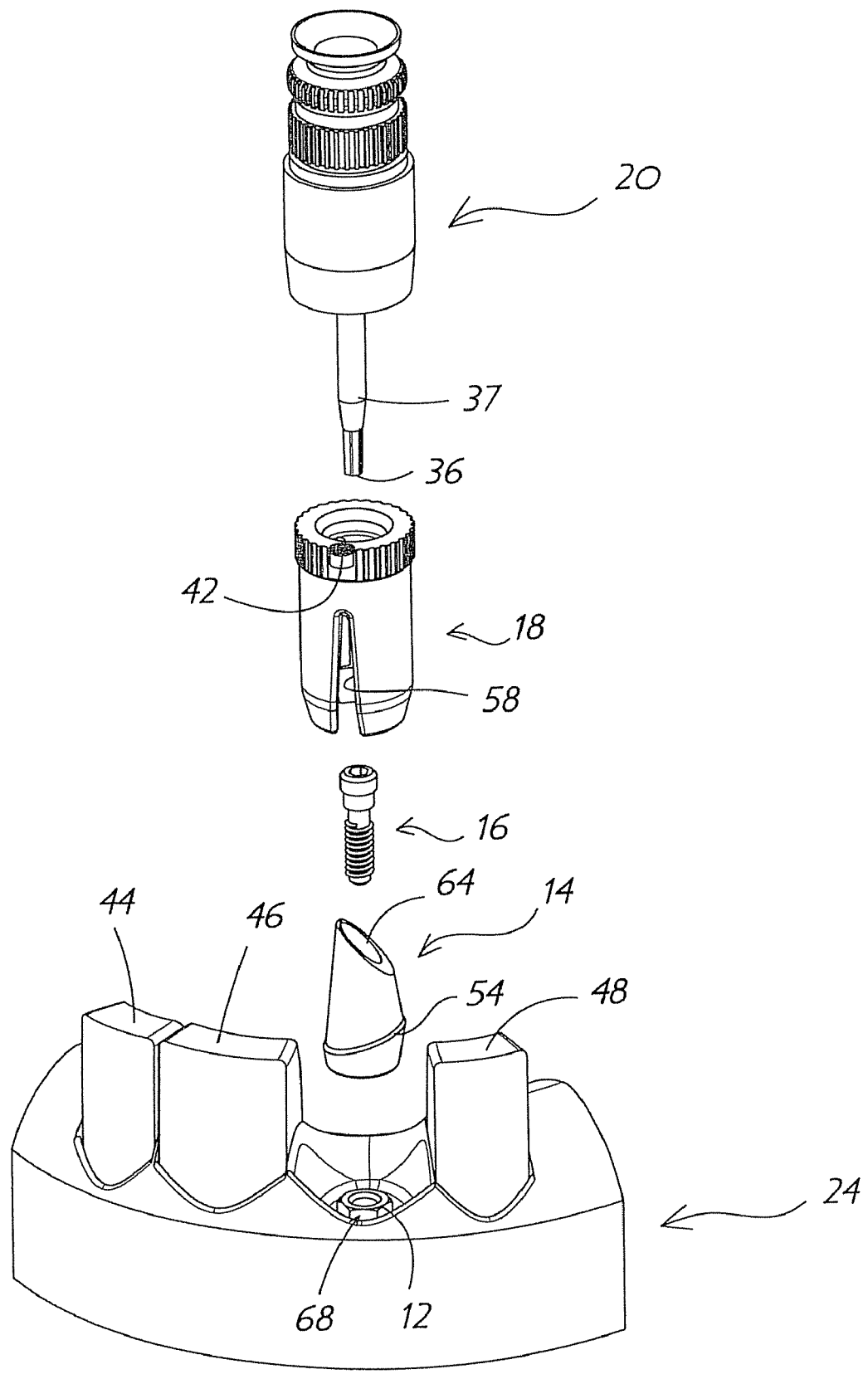
FIG. 15 is an exploded perspective view of the plaster model or the patient jaw showing the implant post, the abutment, the screw, the abutment clip and the screwdriver.

Referring to FIGS. 1-14, there is shown a dental implant system 10 comprising an implant post 12, an abutment 14, an abutment screw 16, an abutment clip 18 in accordance with the present invention, and a screwdriver 20 for securing the various components together. System 10 is used to install a prosthesis, such as artificial tooth 22 (FIG. 6) into the jaw of a patient. In the attached figures, the jaw illustrated may represent a model 24a (FIG. 12) of a patient's jaw that is used for transporting a manufactured abutment 14 and prosthesis 22 from a laboratory to a dental surgeon, or it may be the actual jaw 24b (FIG. 13) into which the implant and abutment are secured.

Figure 1:
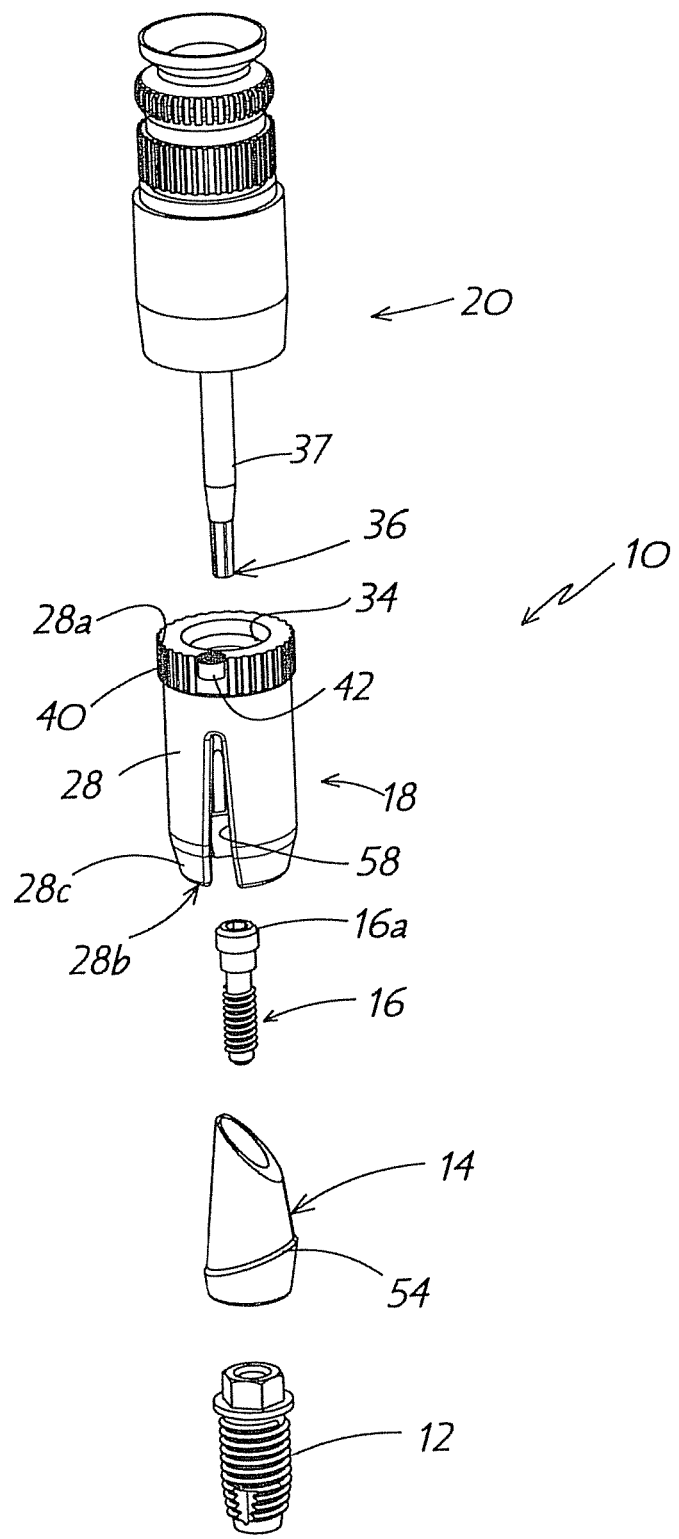
FIG. 1 is an exploded partial perspective view of the dental screwdriver, the abutment clip of the present invention, the screw and abutment into which it is being installed.
Figure 2:
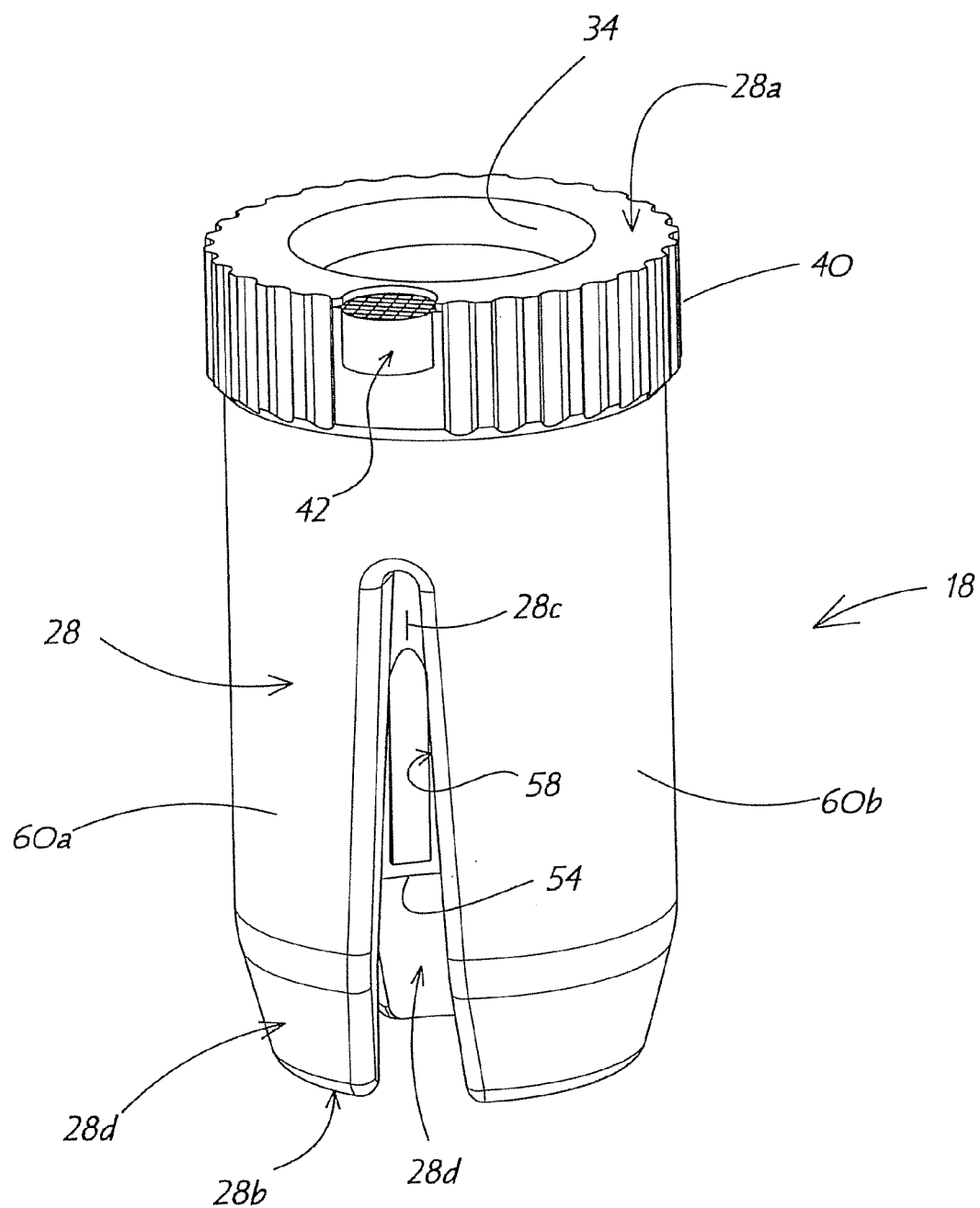
FIG. 2 is a partial perspective view of the abutment clip in accordance with the present invention.
Figure 3:
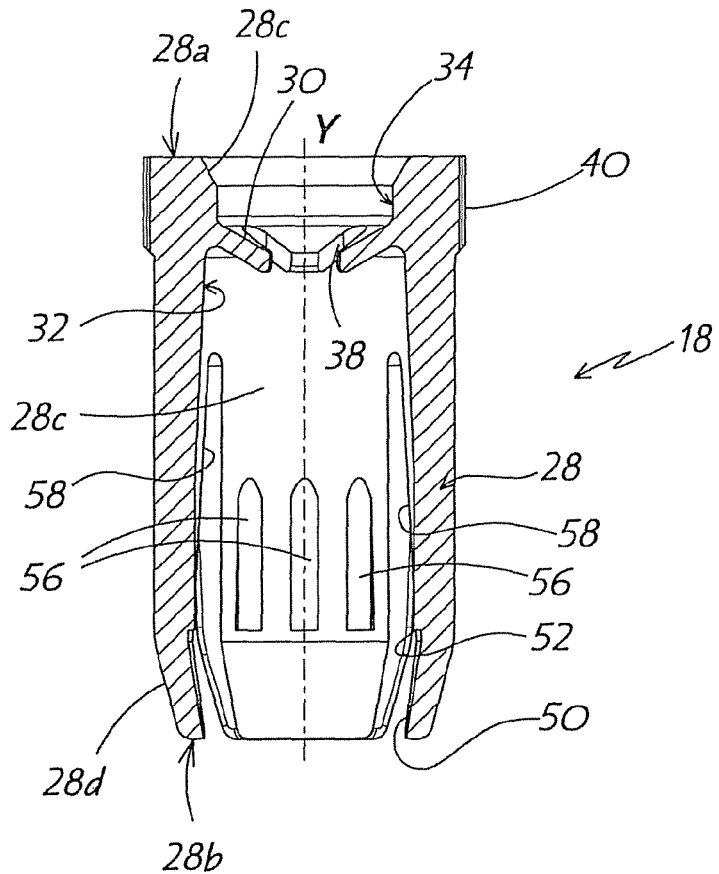
FIG. 3 is a cross-sectional front view of the abutment clip of FIG. 2.
Figure 4:
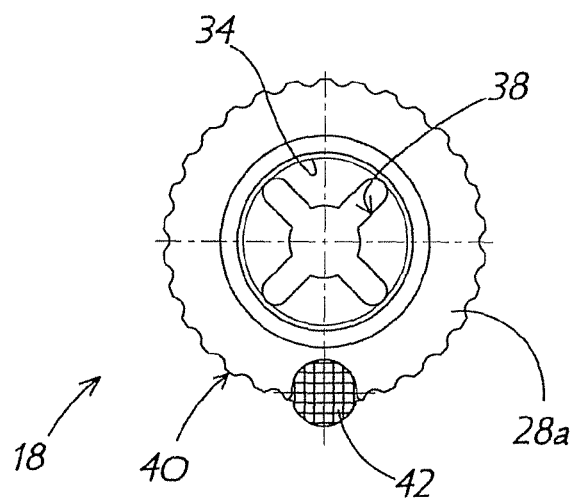
FIG. 4 is a top view of the abutment clip of FIG. 2.

As shown in FIGS. 2-4, and in accordance with a specific feature of the present invention, an abutment clip 18 is provided to enable a dental surgeon to more accurately identify the orientation that abutment 14 has in jaw 24a and to replicate that orientation when the abutment 14 and prosthesis 22 are positioned in the jaw 24b of the patient.

Still referring to FIGS. 2-4, abutment clip 18 comprises a housing having a generally cylindrical peripheral wall 28, an end wall 30 and longitudinal axis "Y". Peripheral wall 28 has a first and a second end 28a, 28b and end wall 30 is positioned intermediate first and second ends 28a, 28b. End wall 30 is however closer to first end 28a than to second end 28b. End wall 30 and peripheral wall 28 surround and define a chamber 32 that is sized to receive abutment 14 therein. End and peripheral walls 30, 28 further define a recess 34 that is sized and shaped so as to direct a tip 36 of screwdriver 20 downwardly and inwardly toward an aperture 38 in end wall 30. Thus, the inner surface 28c of peripheral wall 28 proximate first end 28a includes at least two annular stepped-regions of a progressively narrower diameter. Aperture 38 is configured to receive at least a portion of tip 36 therethrough. In the preferred embodiment of the invention, aperture 38 is shaped to receive the tip of a Phillips screwdriver therein, but it will be understood that aperture 38 could be of any other shape that would specifically engage a differently shaped screwdriver tip such as slotted, hex, Robertson, Pozidriv (® of Phillips Screw Company of Wakefield, Mass.); and Torx (® of Textron Industries, Inc. of Rockford Ill.). First end 28a of peripheral wall 28 also includes a grasping area that enables the dental surgeon to more easily hold the clip 18 against rotation. Grasping area preferably comprises a knurled surface 40 that is provided on the exterior surface of peripheral wall 28 proximate first end 28a. The knurled surface 40 may be an integral part of peripheral wall 28 or may be a separate textured region that is applied over the exterior surface of peripheral wall 28, as shown in FIG. 3.

In accordance with another specific feature of the present invention, first end 28a of abutment clip 18 is provided with one or more position indicators 42 thereon. Indicators 42 preferably are positioned at least partially on both the upper surface and side surface of first end 28a of clip 18 so that the dental surgeon can more easily see the same. Indicators 42 may be any suitable type of marking device such as a shaped detent, a slot, a colored region or a combination of the same. Furthermore, more than one indicator 42 can be provided around the circumference of first end 28a so that the dental surgeon has more than one reference point by which to orient the abutment 14 relative to the jaw 24 or to other teeth 44, 46, 48 that are adjacent the position in jaw 24 where abutment 14 is to be installed.

Still referring to FIGS. 2-4, in accordance with yet another feature of the present invention, clip 18 is provided with an abutment engaging area proximate second end 28b thereof. Abutment engaging area includes an annular region 28d of peripheral wall 28 that tapers inwardly proximate second end 28b. Thus, the diameter of the opening 50 to chamber 32 is narrowed making it more difficult for abutment 14 to slide out of chamber 32. Furthermore, peripheral wall 28 of clip 18 is provided with one or more axial slots 58 that extend from second end 28b inwardly toward end wall 30 thereof. Preferably, more than one slot 58 is provided in peripheral wall 28 so that wall 28 is divided into opposing jaws, such as jaws 60a, 60b shown in FIG. 2. Jaws 60a, 60b are designed to act like pincers that open slightly to engage abutment 14 and then close again to grasp abutment 14 between them. If two slots 58 are provided in peripheral wall 28, then those slots 58 are disposed opposite each other. If three slots 58 are provided in peripheral wall 28 (such as in the version of abutment clip 18 shown in the drawings), then those slots 58 are positioned at equal distances around the circumference of peripheral wall 28.

An annular shoulder 52 is formed in the inner surface 28c of peripheral wall 28 proximate an inner end of tapered region 28d. Annular shoulder 52 is provided to interlock with a shoulder 54 on abutment 14. Inner surface 28c is also provided with a plurality of spaced-apart axial ribs 56. Ribs 56 preferably are formed inwardly of shoulder 52 but do not extend the entire length of chamber 32 up to end wall 30. Ribs 56 are provided to aid in gripping abutment 14 and to retard any rotational motion of abutment 14 within chamber 32.

Figure 5:
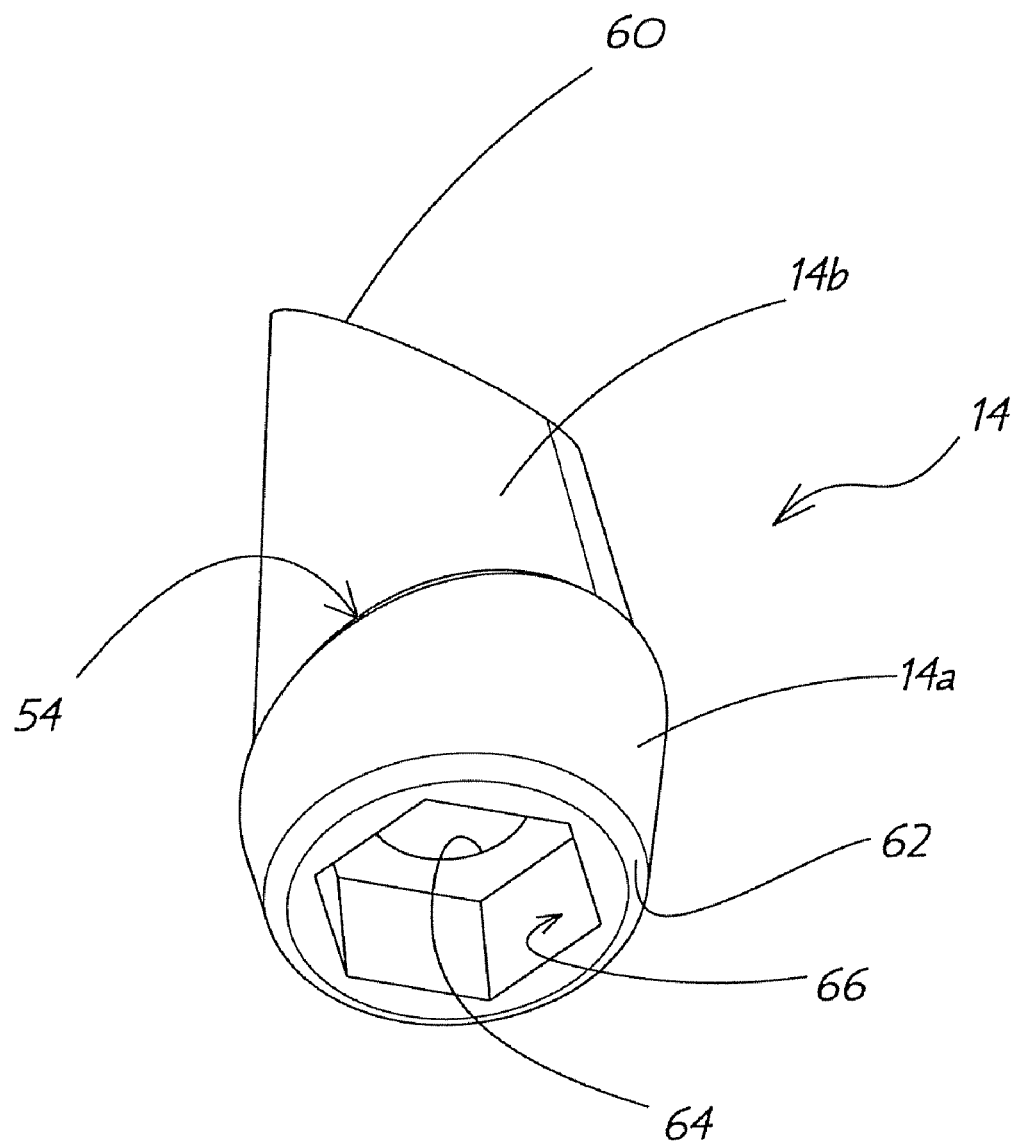
FIG. 5 is a bottom perspective view of an abutment showing a hex-shaped recess for engagement with the implant post.
Figure 6:
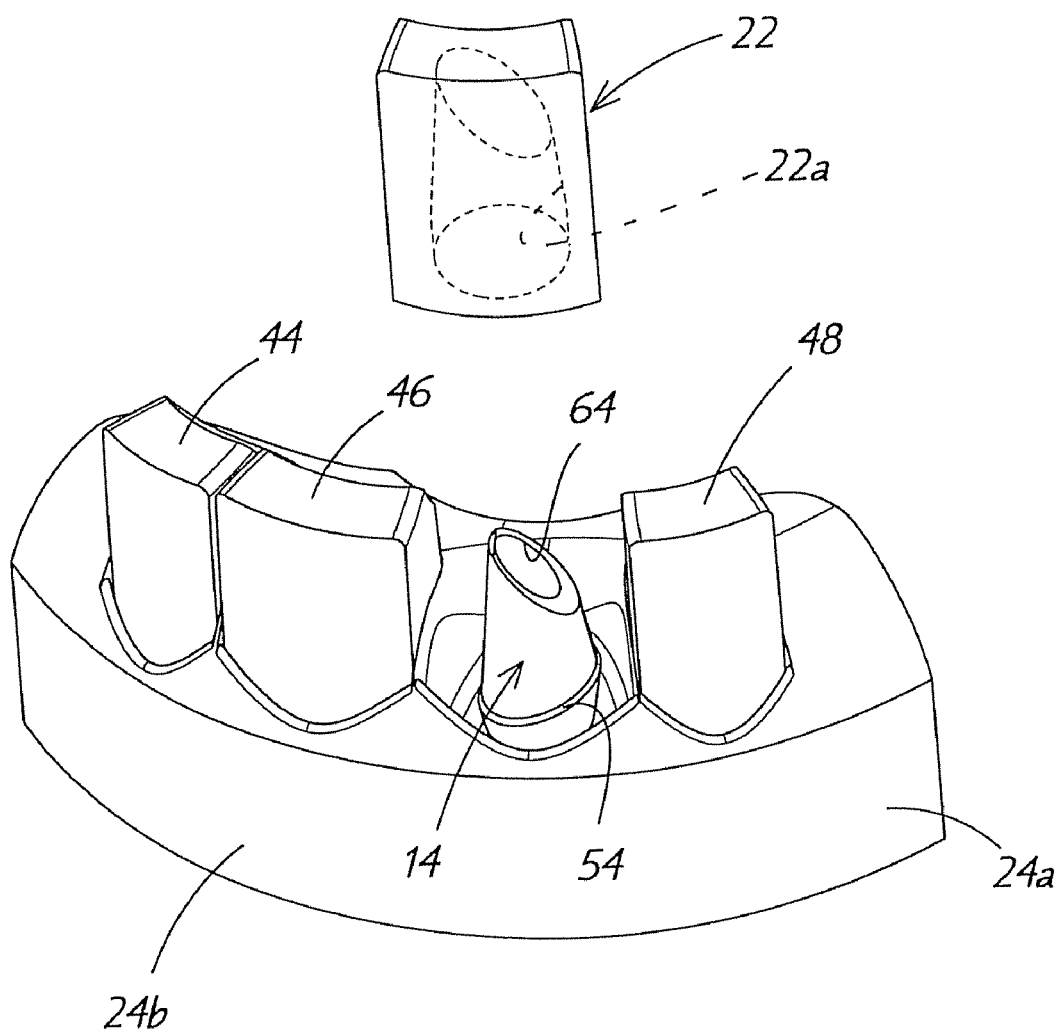
FIG. 6 is a perspective view of a plaster model or the patient's jaw with the abutment secured thereto and the prosthesis removed therefrom.
Figure 7:
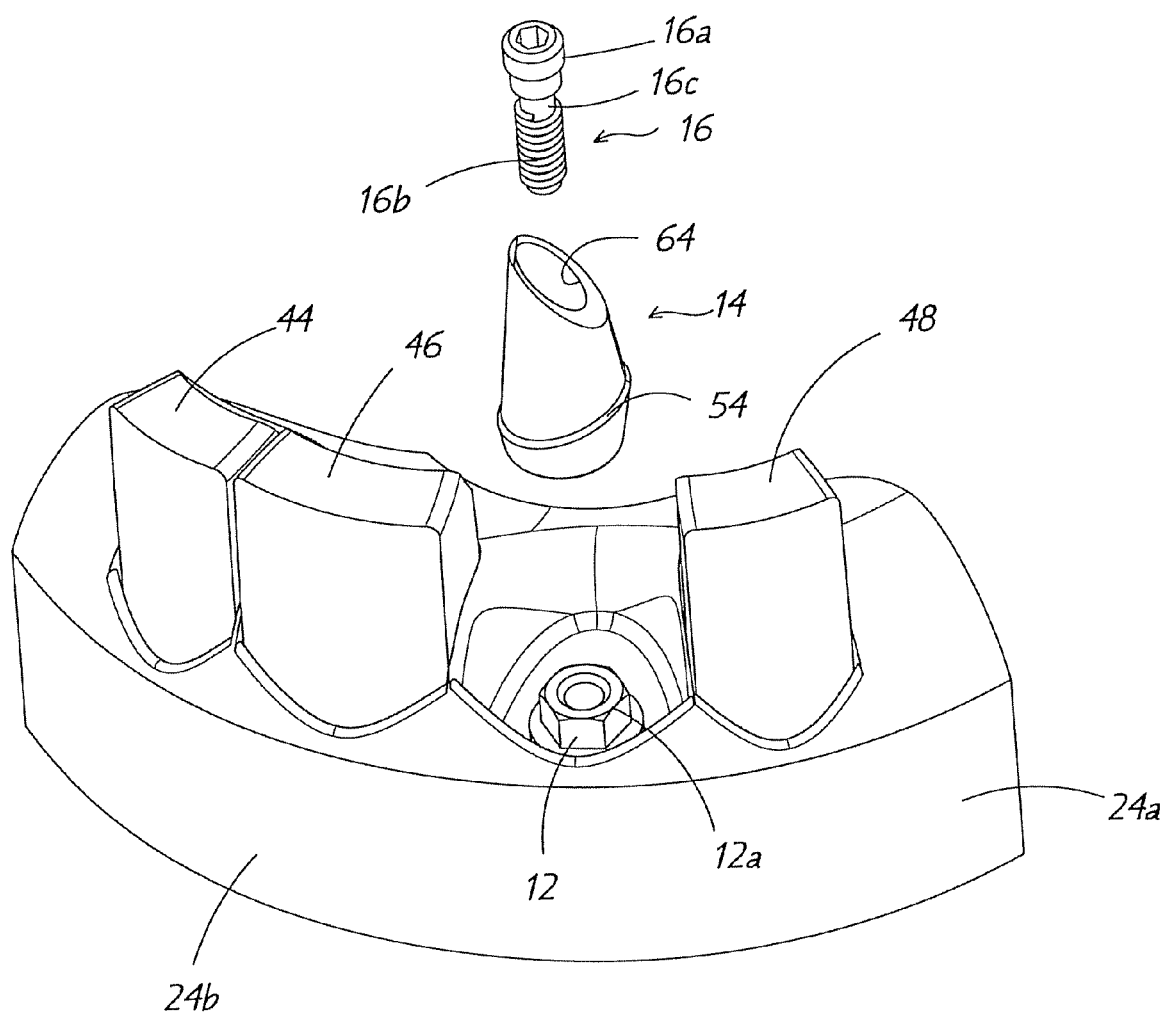
FIG. 7 is a partially exploded perspective view of the plaster model or the patient's jaw showing the abutment, the screw and an implant post.

The abutment clip 18 of the present invention is used to engage and retain the abutment 14. It will be understood that abutment 14, shown in greater detail in FIG. 5, is merely illustrative of any shaped and configured abutment that is engageable by abutment clip 18. Thus, abutment 14 has an upper end 60 and a lower end 62 with a bore 64 extending from the upper to the lower ends 60, 62. Bore 64 is sized to receive screw 16 therethrough. As mentioned previously, abutment 14 also includes a shoulder 54 formed on an annular lower region 14a that is of a greater diameter than the upper region 14b. Lower end 62 is also provided with a shaped recess 66 to receive and engage the head 68 of implant post 12 therein. FIG. 5 illustrates recess 66 as hexagonally shaped so that it may engage with a hexagonally shaped head of implant post 12. It will be understood that recess 66 may be of a different configuration so as to engage differently shaped implant post heads. So, for example, some dental implant systems have square implant post heads and in that instance, the abutment to be used therewith will have a square recess in its lower end. The overall shape and size of abutment 14 is designed and custom built by the dental manufacturer to correctly orient and support the prosthesis 22 that is to be installed thereover. Consequently, abutment clip 18 will engage a variety of differently shaped abutments 14 and retain the same within chamber 32. However, because the size of the abutment 14 may vary with the diameters of upper and lower regions 14b, 14a thereof being larger or smaller as necessary, the dental surgeon will have a range of different sized abutment clips 18 to engage differently sized abutments 14, and will select the appropriate clip for the job.

Figure 8:
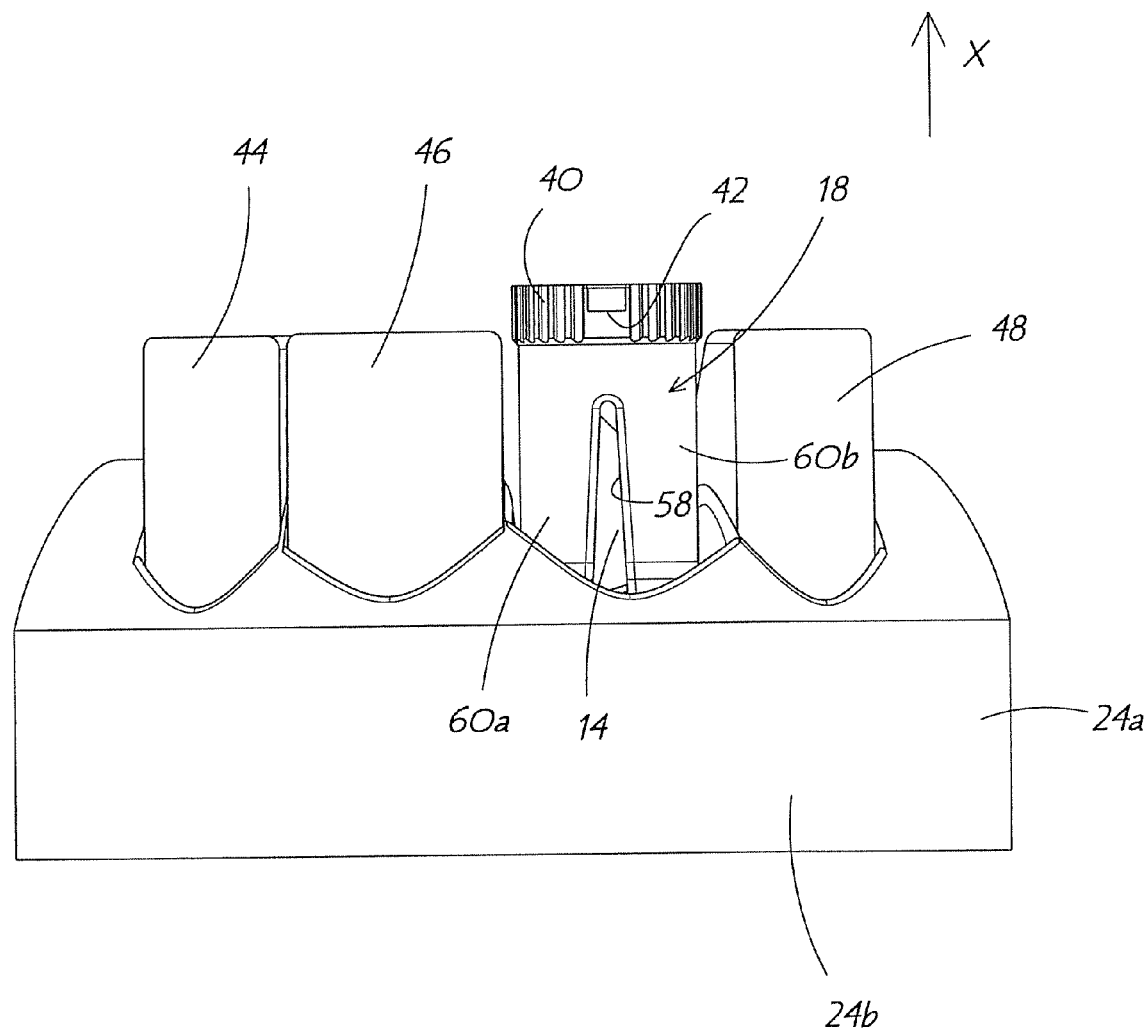
FIG. 8 is a front view of the plaster model or the patient's jaw with the abutment clip in engagement with the abutment.
Figure 9:
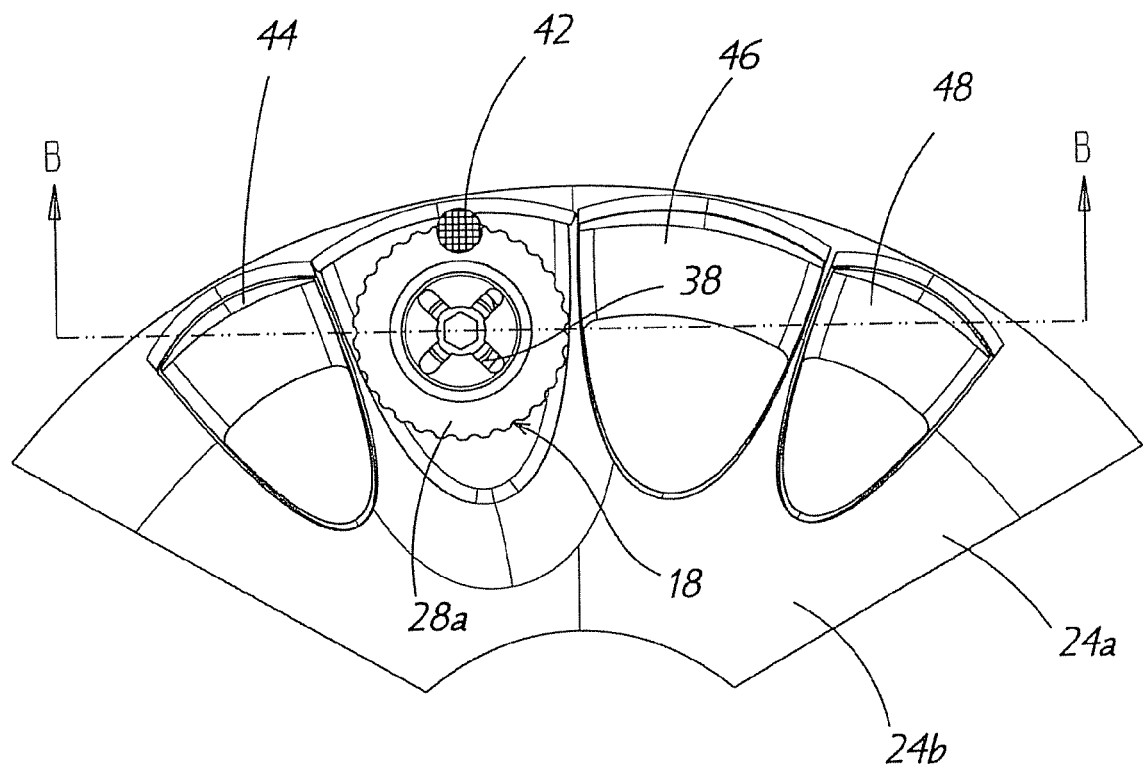
FIG. 9 is a top view of the plaster model or the patient jaw with the abutment clip in engagement with the abutment.
Figure 10:
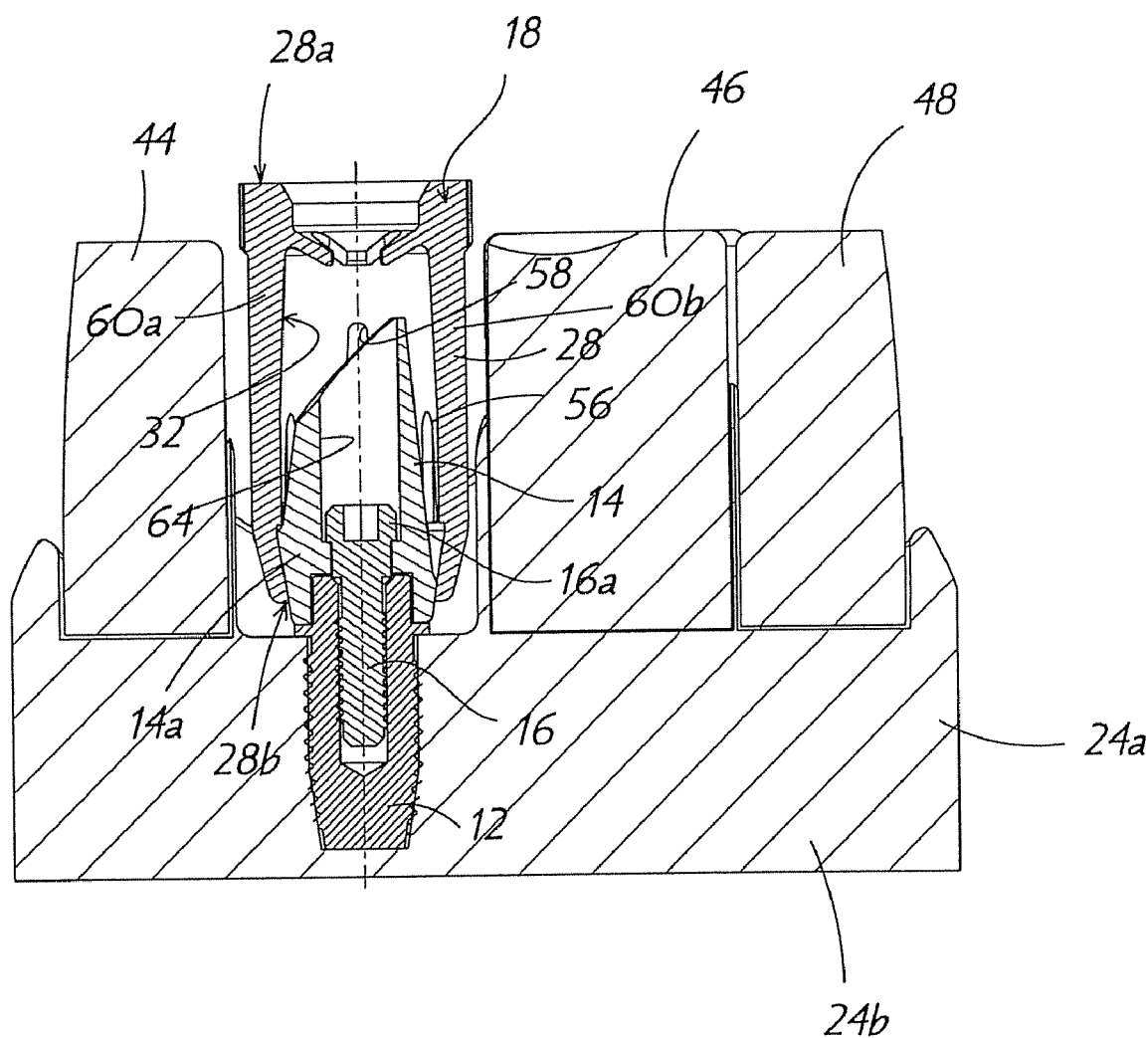
FIG. 10 is a cross-sectional view of the plaster model or the patient jaw through line B-B of FIG. 9.
Figure 11:
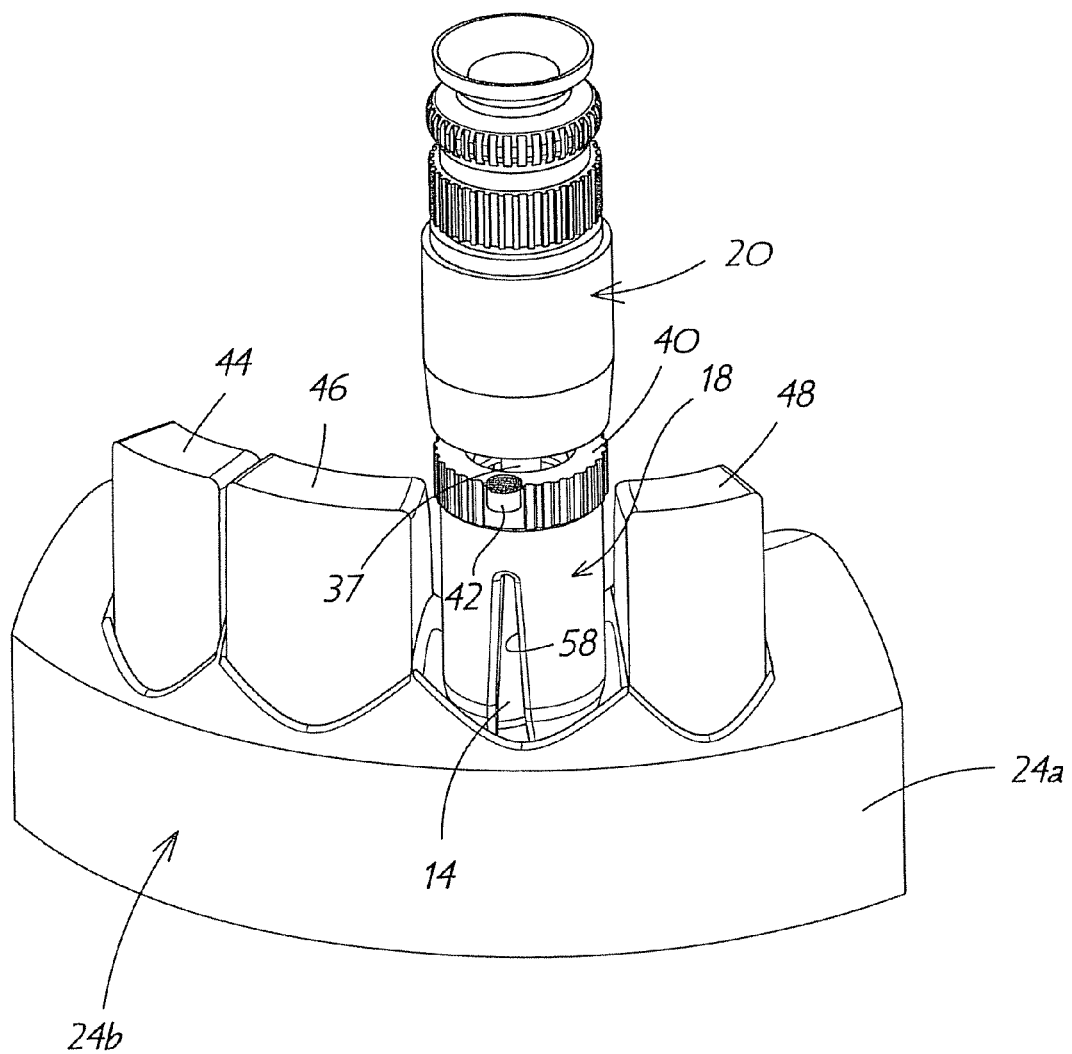
FIG. 11 is a perspective view of the plaster model or the patient jaw showing the screwdriver engaging the abutment and abutment clip.

The abutment clip 18 of the present invention is used in the following manner. When the dental surgeon is sent the plaster model of the patient's jaw, the model (shown in FIGS. 6&7) has abutment 14 secured to jaw 24a via a screw 16 and an implant post 12a. Implant post 12a is substantially identical to the bolt 12 that has been previously implanted in the patient's jaw 24. The prosthesis 22 will typically be positioned over abutment 14, but is not physically secured thereto. The dental surgeon will remove prosthesis 22, take the appropriately sized abutment clip 18 and slide the same downwardly over abutment 14 (FIGS. 8-10). At this point, the surgeon will manipulate abutment clip 18 until indicator 42 is in a position that he can use to serve as a reference point for later installation of the abutment in the patient's mouth. That position will be noted by the surgeon in any manner appropriate to himself. At this stage, abutment clip 18 is engaged with abutment 14 in such a manner that shoulder 52 on clip 18 is interlocked with shoulder 54 on abutment 14. Furthermore, the jaws 60a, 60b are firmly in engagement with the lower portion 14a of abutment 14. Ribs 56 abut lower portion 14a and abutment 14 is tightly retained within abutment clip 18. At this point, abutment clip 18, screw 16 and abutment 14 form an abutment assembly that may be selectively engaged with implant post 12 or disengaged therefrom. The recess 66 on abutment 14 is presented at the second end 28b of abutment clip 18 for such engagement with implant post 12.

The dental surgeon grasps knurled portion 40 of abutment clip 18 and using a screwdriver 20, inserts the tip 36 and a portion of the shaft 37 thereof through aperture 38 in end wall 30, through bore 64 of abutment 14 and into engagement with head 16a of screw 16. It will be understood that while a dental screwdriver 20 is illustrated herein, any other suitable screwdriver, such as a jeweler's screwdriver can be used. The surgeon holds the knurled portion 40 of clip 18 to ensure that clip 18 and abutment 14 do not rotate when screw 16 is rotated as the position of abutment 14 in clip 18 needs to be maintained. Once screw 16 is loosened, the combined abutment 14, screw 16 and abutment clip 18 is removed from the jaw 24a of the plastic model.

The dental surgeon then positions the combined abutment 14, screw 16 and clip 18 in place in the patient's jaw 24b. In order to do this, he lowers clip 18 onto implant post 12 (FIG. 7) so that the head of said bolt 12 is received into recess 66 of abutment 14. Indicator 42 is used to orient abutment clip 18 in exactly the same position relative to teeth 44, 46, 48 that was noted on the plaster model. If the surgeon does not think the position is correct, the combined clip 18, abutment 14 and screw 16 is lifted off implant post 12 and is rotated slightly and re-engaged with bolt 12. Once the position of abutment clip 18 is correct, the screwdriver tip 36 is engaged with screw 16. The surgeon grips knurled portion 20 of clip 18 to ensure there is no rotation of the same when screwdriver 20 is activated. Screw 16 is rotated by screwdriver 20 so that the threads 16b on the shaft 16c thereof threadably engage the internal threads of implant post 12. Once abutment 14 is secured, screwdriver 20 is disengaged and an X-ray is taken of the patient's mouth to ensure that abutment 14 is in exactly the correct position and that it is fully seated on implant post 12. If this is found to be true, then screw 16 is torqued to the manufacturer's specifications in the known manner. The surgeon then removes abutment clip 18 by grasping knurled portion 40 and pulling clip 18 off of abutment 14 in the direction of arrow "X" (FIG. 8).

The dentist will then take the prosthesis 22 and apply a small amount of cement to the abutment 14 and/or interior of a hole 22a in prosthesis 22. The prosthesis 22 is then slidingly engaged over abutment 14 so that abutment 14 is received within hole 22a.

In the foregoing description, certain terms have been used for brevity, clearness, and understanding. No unnecessary limitations are to be implied therefrom beyond the requirement of the prior art because such terms are used for descriptive purposes and are intended to be broadly construed.

Moreover, the description and illustration of the invention are an example and the invention is not limited to the exact details shown or described.

The invention claimed is:

1. A method of installing a prosthesis in a patient's jawbone;
where the method includes the steps:
locating a reference point on a feature of a one of the patient's jawbone and teeth;
placing an abutment clip over an implant post previously installed in the patient's jawbone;
aligning a position indicator on the abutment clip with the located reference point;
positioning an abutment on a replica of the previously installed implant post that forms part of a plaster model;
locating a reference point on a feature of a plaster model of the patient's jawbone and teeth that corresponds with the located reference point on the corresponding feature on the one of the patient's jawbone and teeth; and
placing the abutment clip over the abutment.

2. The method as defined in claim 1, further including the step of:
manipulating the abutment clip to align the position indicator on the abutment clip with the reference point on the plaster model.

3. The method as defined in claim 1, further comprising the step of selecting an appropriately sized abutment clip from a set of abutment clips of various sizes prior to the step of placing the abutment clip over the abutment.

4. The method as defined in claim 1, further including the step of sliding the selected abutment clip over the abutment when the abutment is secured by a dental screw to the replica of the implant post on the plaster model.

5. The method as defined in claim 4, wherein the step of sliding the abutment clip includes sliding the abutment clip downwardly until jaws on the abutment clip engage a shoulder on the abutment.

6. The method as defined in claim 5, further comprising the step of unscrewing the dental screw to release the abutment from engagement with the replica of the implant post while the abutment is retained in the jaws of the abutment clip.

7. The method as defined in claim 6, further including the step of transferring the abutment from the plaster model to the patient's jawbone while engaged with the abutment clip.

8. The method as defined in claim 7, further including the steps of:
inserting a screwdriver through an aperture in the abutment clip to engage the dental screw securing the abutment to the replica of the implant post;
rotating the screwdriver in a first direction to disengage the dental screw from the replica of the implant post; and
using the screwdriver to transfer the abutment clip, dental screw and abutment from the plaster model to the patient's jawbone.

9. The method as defined in claim 8, further comprising the step of sliding the abutment downwardly over a head of the implant post previously installed in the patient's jawbone while the abutment is retained in the jaws of the abutment clip and the screwdriver is engaged with the dental screw disposed in the abutment.

10. The method as defined in claim 9, further comprising the step of rotating the abutment about the head of the implant post previously installed in the patient's jawbone until the positioning indicator on the abutment clip is in the correct position with reference to the feature on the patient's jawbone.

11. The method as defined in claim 10, further comprising the step of engaging the dental screw in the implant post installed in the patient's jawbone to seat the dental screw while maintaining the correct positioning of the abutment by way of the abutment clip.

12. The method as defined in claim 11, further comprising the step of torquing the dental screw to a tolerance indicated by a manufacturer of the screw.

13. The method as defined in claim 11, wherein the steps of rotating the screw to either remove the abutment or install the abutment further includes the step of grasping a knurled surface on the abutment clip to retard rotation of the abutment relative to the feature on the plaster model or to the feature on the patient's jawbone.

14. The method as defined in claim 1, further comprising the step of attaching a prosthesis to the abutment once installed on the implant post in the patient's jawbone.

15. The method as defined in claim 14, further comprising the step of removing the abutment clip from over the abutment prior to the step of attaching the prosthesis to the abutment.

16. The method as defined in claim 15, further comprising the steps of:
grasping the abutment clip by way of a knurled surface; and
pulling upwardly to disengage the abutment clip from the abutment.

17. The method as defined in claim 14, wherein the step of attaching the prosthesis to the abutment includes the step of applying a cement to one or both of the abutment and an interior surface of the prosthesis.

18. A method of installing a prosthesis in a patient's jawbone comprising the steps of:
installing an implant post in the patient's jawbone;
creating a plaster model of the patient's jawbone;
engaging an abutment over a replica of an implant post located on the plaster model;
sliding an abutment clip over the abutment that is secured by a screw to the replica of the implant post;
locating a reference point on a feature of the plaster model that corresponds to a feature on the patient's jawbone;
noting the position of a position indicator on the abutment clip with respect to the feature on the plaster model;
inserting a tip of a screwdriver through an aperture in an end wall of the abutment clip to engage the screw;
rotating the screw so as to disengage the abutment from the replica of the implant post;
detaching the engaged abutment clip, screw and abutment from the plaster model;
positioning the engaged abutment clip, screw and abutment over a head of the implant post previously installed in the patient's jawbone;
locating the feature on the patient's jawbone that corresponds to the feature on the plaster model;
aligning the position indicator on the abutment clip in the previously noted position relative to the feature on the patient's jawbone;
rotating the screw with the screwdriver in the opposite direction so as to threadably engage the same with an internally threaded bore of the implant post in the patient's jawbone;
removing the abutment clip from over the abutment; and
attaching the prosthesis to the abutment.

19. The method as defined in claim 18, wherein the step of attaching the prosthesis to the abutment includes the step of applying a cement to one or both of the abutment and an interior surface of the prosthesis.

20. The method as defined in claim 18, further comprising the step of selecting an appropriately sized abutment clip from a set of variously sized abutment clips prior to the step of sliding the abutment clip over the abutment.

21. The method as defined in claim 18, wherein the step of rotating the screw to either remove or insert the abutment includes the step of grasping a knurled surface on the abutment clip to retard rotation of the abutment.

22. A method of installing a prosthesis in a patient's jawbone; where the method includes the steps:
   locating a reference point on a feature of a one of the patient's jawbone and teeth;
   placing an abutment clip over an implant post previously installed in the patient's jawbone; and
   aligning a position indicator on the abutment clip with the located reference point, wherein the position indicator forms a part of the abutment clip;
   positioning an abutment on a replica of the previously installed implant post that forms part of a plaster model;
   locating a reference point on a feature of a plaster model of the patient's jawbone and teeth that corresponds with the located reference point on the corresponding feature on the one of the patient's jawbone and teeth; and
   placing the abutment clip over the abutment.

* * * * *